United States Patent [19]

Gork et al.

[11] Patent Number: 5,036,001
[45] Date of Patent: Jul. 30, 1991

[54] METHOD FOR SUPPLYING FOODSTUFF SAMPLES FOR MICROBIOLOGICAL TESTING

[75] Inventors: Fritz-Peter Gork, Hattersheim; Klaus-Dieter Müller, Riedstadt; Doris Schweitzer, Wallau, all of Fed. Rep. of Germany

[73] Assignee: Lufthansa Service GmbH, Fed. Rep. of Germany

[21] Appl. No.: 328,589

[22] PCT Filed: Mar. 29, 1988

[86] PCT No.: PCT/EP88/00261
§ 371 Date: Jan. 19, 1989
§ 102(e) Date: Jan. 19, 1989

[87] PCT Pub. No.: WO88/07710
PCT Pub. Date: Oct. 6, 1988

[30] Foreign Application Priority Data

Mar. 31, 1987 [DE] Fed. Rep. of Germany ....... 3710663
Jun. 23, 1987 [DE] Fed. Rep. of Germany ....... 3720733

[51] Int. Cl.⁵ .......................... C12Q 1/00; B25J 11/00
[52] U.S. Cl. .................................. 435/31; 73/864.24; 435/291; 901/44
[58] Field of Search ............................ 435/29, 31, 291; 73/864.24; 364/496; 901/44; 426/231

[56] References Cited

U.S. PATENT DOCUMENTS

| 4,593,820 | 6/1986 | Antonie et al. | 901/44 |
| 4,720,463 | 1/1988 | Farber et al. | 435/291 |
| 4,757,437 | 7/1988 | Nishimura | 364/496 |

*Primary Examiner*—George Yeung
*Attorney, Agent, or Firm*—Lowe, Price, Leblanc and Becker

[57] ABSTRACT

Methods for supplying a foodstuff sample for microbiological testing comprise supplying the sample in a plastic bag, adding physiological nutrient solution to the sample in a specified weight ratio, mechanically comminuting and homogenizing the contents of the bag, and removing a partial quantity of the contents of the bag by means of pipette via a filter as sample liquid. The methods further comprise injecting the same liquid onto at least one nutrient medium situated in a petri dish and inserting the injected petri dish into an incubator. In the communution and homogenization of the contents of the bag, the bag is clamped shut and pressed between a fixed jaw and two jaws which oscillate alternately. In the injection of the nutrient medium, the sample liquid is injected in a spiral shape onto the nutrient medium. Additionally, a laboratory robot system is employed.

14 Claims, 1 Drawing Sheet

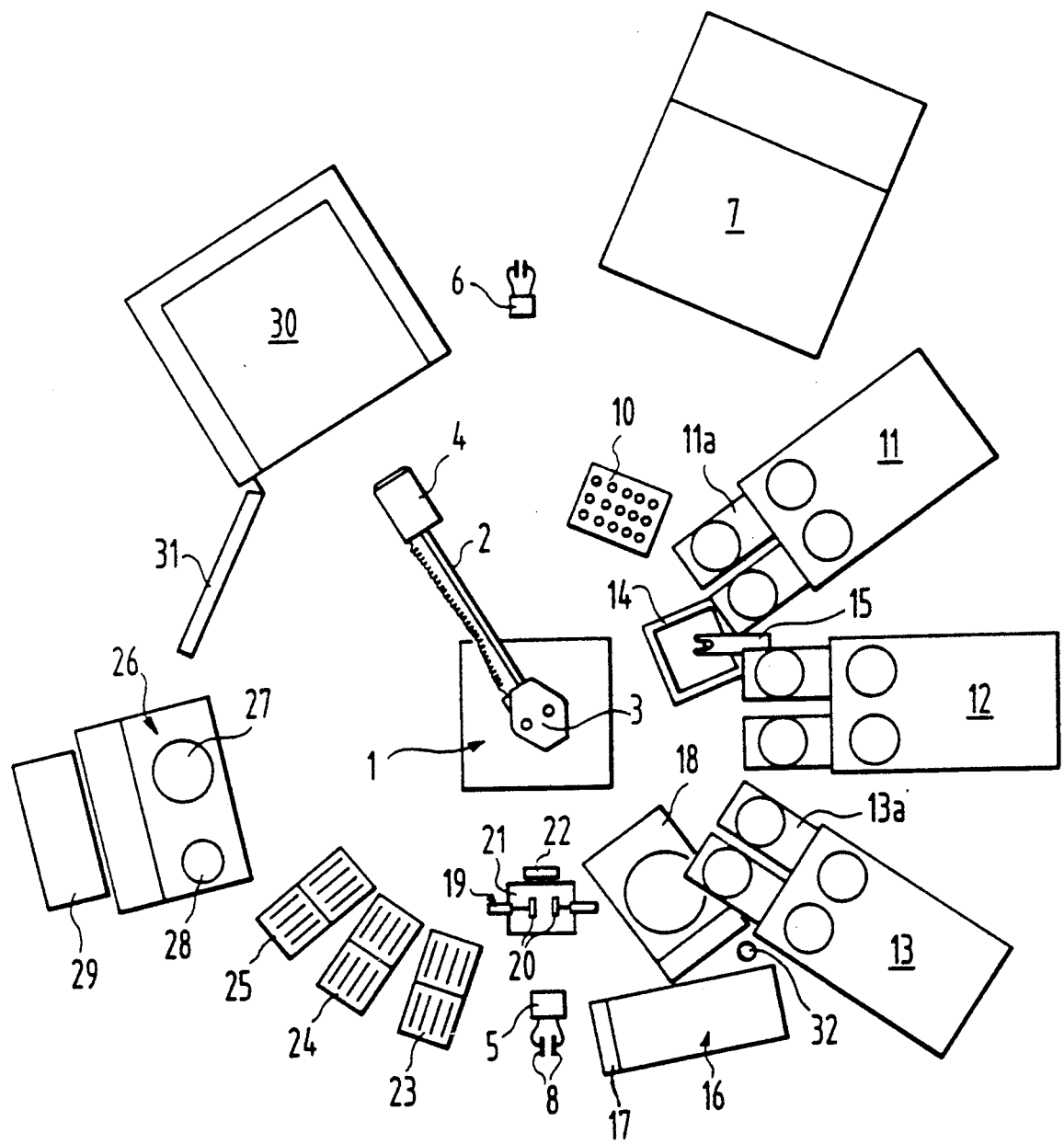

METHOD FOR SUPPLYING FOODSTUFF SAMPLES FOR MICROBIOLOGICAL TESTING

The invention relates to a method for supplying foodstuff samples for the microbiological testing.

To date, microbiological examinations were carried out exclusively by hand. This is justifiable, when few samples are concerned. However, in the foodstuffs industry, samples have to be examined frequently and in large numbers with regard to the bacillus factor. A further complication is that in microbiological examinations, work must be carried out under sterile conditions, and too great a time must not elapse from the delivery of the samples up to installation in the incubator, because otherwise owing to the multiplication of the bacilli even at room temperature, the result of the examination would be falsified.

The invention is based on the problem of developing the testing method of the type indicated in the introduction such that it can run automatically after preparation of the samples up to installation of the injected nutrient media into the incubator.

This problem is solved according to the invention.

An essential feature of the method according to the invention is the use of a laboratory robot system with a handling robot and a programmable control unit. Such a system is indeed already known as a universal system to carry out various laboratory operations (laboratory robot system of the firm Zymark Corporation, Hopkinton, MA USA). However, this has never until now been installed and used to carry out the relatively complex microbiological examinations. The result which is aimed for according to the invention is only achieved in that the laboratory robot system is used in combination with two further quite specific items of laboratory apparatus which are likewise already known per se, namely the so-called stomacher and the so-called spiral-plater. The stomacher allows the comminution and homogenization of samples, which are contained in plastic bags, with the plastic bag closed. Through this it becomes possible to leave the samples, which are to be examined, in plastic bags during the entire examination. This, in turn, is a prerequisite for the fact that the samples can be handled individually by the laboratory robot, without the samples or residues of samples hereby coming into contact with each other, whereby the result of the examination would be falsified. The microbiological examination further requires that sample liquid with differing concentration is injected out from each sample onto the nutrient medium. The spiral-plater, with which the sample liquid is injected onto the rotating nutrient medium through a nozzle which is moved in radial direction, i.e. in a spiral shape and hence in one working step in differing concentration, creates the prerequisite for the fact that this process can also be handled by the laboratory robot system, which would scarcely be possible with a multiple-stage injecting out, e.g. with sample liquids of different concentrations, owing to the too high complexity of such a process and owing to too great an expenditure of time. In all, it is achieved by the method according to the invention that in particular samples of foodstuffs can be examined fully automatically in large numbers. It is merely necessary to place the samples, which have been removed for example in the foodstuffs factory, in the plastic bag in readiness. They are then treated fully automatically, according to the method of the invention, up to installation of the ready injected nutrient media, in petri dishes, into the incubator.

In one embodiment of the new method according to the invention, the accurate dosing of the samples, hitherto performed, which would only be able to be carried out by the robot with difficulty, is not necessary. The samples which have only been estimated approximately as regards their weight, can be treated just as they arrive after removal. The desired precise weight ratio between the sample and the physiological nutrient solution is produced through corresponding dosing of the nutrient solution, which is preferably able to be carried out easily automatically as a time-dependent, but also volumetric dosing. Here, the control unit takes charge of the evaluation of the weighing of the sample and the calculation of the necessary quantity of nutrient solution.

The another embodiment, the new method makes possible the further acceleration thereof through the "nesting" of sections of the process, whereby the stomacher is very soon freed for a new sample. In addition, the clean removal of the plastic bags of which the contents have been evaluated, is ensured by simply dropping into the waste opening.

A further embodiment acts in the same direction. The mechanical screen surrounding the pipette acts as a filter, through which only sample liquid can pass. Of course, the pipette must be cleaned and carefully sterilised after each removal process. Through the activation of the disinfection and cleaning bath by ultrasonics, at the same time a mechanical cleaning in particular of the screen of the pipette is achieved, whereby one is saved from exchanging a filter after each removal process. To save time, the suction pipette can be allowed to drain, whilst the stomacher is in operation.

The spiral-plater, known per se, has a built-in dosing pump. In the conventional use within examinations which are carried out by hand, the sample liquid which is to be injected out is sucked in by means of the backwardly-running dosing pump through the injection nozzle of the spiral-plater. Normally, two nutrient media are injected in a spiral shape with the sample liquid from one sample. Until now, this meant two suction processes. In one embodiment of the new method, sample liquid for the spiral-plater is only sucked in once, and the injection of several nutrient media is nevertheless possible, which further complies with the automatic carrying out of the method.

The method may include a step for the reliable mutual separation of the samples. It is likewise carried out automatically, controlled by the control unit.

An essential prerequisite for the automatic running of the examination is a reliable handling of the filled plastic bags by the laboratory robot. This is ensured particularly well when the laboratory robot for the handling of the plastic bags uses a hand in. On transportation, the plastic bag is clamped between the clamping jaws. To open the bag, the openings in the clamping jaws are acted upon with negative pressure and the clamping jaws are moved apart. The openings can also remain acted upon with negative pressure with the clamping jaws in closed state. Then the plastic bags are secured particularly reliably.

In the course of an examination, each plastic bag has to be transported several times and in so doing has to be deposited so as to be accurately positioned at its destination, e.g. on the scales or in the stomacher or in the holding device. In order that this is successful with accuracy, unimpaired by inherent movements of the bag, the manner of procedure according to claim 10 has proved to be advantageous. Through the opening of the plastic bag during the intermediate stop, the plastic bag is stabilised and oscillation movements of the bag cease.

Usually in microbiological examinations, specific nutrient media are additionally injected with the sample liquid, but only in a fixed concentration. To save nutrient media, it is usual to inject each nutrient medium several times with different samples—of course at different sites, e.g. sectors thereof. This injection can advantageously take place within the framework of the method according to the invention.

The petri dishes with fresh nutrient medium, and namely both those for the spiral injection and also those for the multiple injection, are expediently kept ready for automatic handling. In so doing, the laboratory robot always finds the individual petri dish at the same location, which is important for an automatic running of the process which is as simple as possible. Accommodation in a stack, moreover, saves space. In addition, the stack magazines can be replenished during the running of the examination, without disturbance thereof.

As operations must be carried out at all locations under scrupulously sterile conditions, the petri dishes are closed with lids in the conventional manner. It has proved to be difficult to also leave the removal and replacement of the lids to the laboratory robot itself.

The invention with further advantageous details is explained below by means of an example embodiment which is represented diagrammatically. The single figure shows in diagrammatic plan view a laboratory arrangement for the automatic microbiological examination of samples of foodstuffs.

The entire examination arrangement, represented in the single figure, is situated on a large table plate and comprises several individual items of apparatus. In the centre of the arrangement is a laboratory robot 1. This comprises a horizontal arm 2, which stands away from a vertical column 3. The arm is adjustable as regards its height on the column 3 and through rotation of the column 3 about its vertical central axis in horizontal direction is able to be oriented in both directions over a circular arc of somewhat more than 360°. In addition, the arm 2 can be displaced with respect to the column 3 in its longitudinal direction, so that its free end assumes differing distances from the column 3. The figure shows the arm 2 in a partially extended position. At the free end, the arm 2 has a drive unit 4, with which different robot hands, which are movable in each case in several degrees of freedom, are able to be coupled through an insertion process. In the method according to the invention, operations are carried out with two different robot hands 5 and 6, which are to be explained in further detail.

The laboratory robot 1 belongs to a laboratory robot system which additionally comprises a control unit 7, based on a microprocessor, with a keyboard and a screen (not shown in further detail). The control unit is able to be programmed by the user, and controls the laboratory robot 1 and all further items of laboratory apparatus taking part in the examination, in accordance with the programme.

The items of laboratory apparatus taking part in the examination are arranged in a circle around the laboratory robot, so that they can be reached by the robot hand. Amongst the items of laboratory apparatus is a hole magazine 10 with a plurality of vertical holes arranged in a rectangular grid, which holes are in each case equipped with a disposable suction pipette before commencement of an examination series. The disposable suction pipettes can be removed individually out of the hole magazine 10 by the robot 1 by means of the hand 6. The control unit 7 is able to be programmed by means of a sub-programme such that it notes the hole out of which a suction pipette was respectively last taken, and guides the robot hand to the next respective, still filled, hole on the following removal.

Three similar stack magazines 11, 12 and 13 follow the hole magazine 10 in clockwise direction, which stack magazines are to hold petri dishes, in which there are nutrient media. Each stack magazine contains the petri dishes, which are closed by lids, in two stacks. Associated with each stack at the lower end there is a slider. e.g. 11a, which on actuation, controlled by the control unit 7, advances the respectively lowermost petri dish of the stack into the range of action of the robot 1. The magazines 11 and 12 contain petri dishes, the nutrient medium of which is divided into four sectors by cross-pieces in the base of the petri dishes. They are intended for the so-called drop-plating, in which each sector of the nutrient medium is injected with a drop of sample liquid from a different sample in each case. The magazine 13 contains normal petri dishes without cross-pieces, and a correspondingly continuous nutrient medium, which is intended for the so-called spiral-plating, in which sample liquid is injected out in a spiral shape onto the nutrient medium.

Between and in front of the two stack magazines 11 and 12, there is an open container 14 with a disinfection and cleaning bath, which is activated by ultrasonics. Adjacent to the container 14, a drip support 15 is arranged, which is to be explained in further detail.

Following the stack magazine 13 in circumferential direction is a so-called stomacher 16. This is an apparatus known per se for the comminution and homogenization of samples, which are situated in plastic bags. At the left-hand end, the stomacher 16 has a shaft 17 which is able to be closed by a flap. The plastic bags are inserted from above into the opened shaft, where, after the automatic closure of the shaft flap, brought about by means of a motor or a hydraulic cylinder, they are pressed between a fixed jaw and two jaws which lie adjacent to each other and which are moved alternately back and forth.

In front of the stomacher 16 there is an electronic scales 18. Following the stomacher 16 in circumferential direction is a mounting, not represented in further detail, for one hand 5 of the robot. The hand 5 is intended for the handling of plastic bags filled with samples. For this, it has two clamping jaws 8, between which the upwardly open plastic bags can be grasped and clamped at their upper rim. In the clamping jaws 8, openings are provided which are able to be acted upon by negative pressure in a manner not shown in further detail. When these openings are acted upon by negative pressure, the walls of the bags remain adhered to the respective jaw, so that the bags can be opened by moving the clamping jaws 8 apart, and nevertheless do not drop out of the clamping jaw.

Between the mounting for the hand 5 and the robot 1, there is a fixed holding station 19 for the plastic bags, which in an analogus manner to hand 5 has two clamping jaws 20 respectively with negative pressure openings. Under the mounting 19 there is a waste opening 21 in the table plate. In radial direction immediately adjacent to the stationary holding station 19 at the edge of the waste opening 21 a stripper 22 is fixedly mounted.

Following the mounting for the hand 5 in circumferential direction are three similar bag magazines 23, 24 and 25, in each case radially aligned. Three bag magazines are shown merely by way of example. In practice, in particular, more may also be present. In the arrangement to be found in practical testing, finally five bag magazines were provided. Each bag magazine has several upwardly open openings, elongated in radial direction, into which plastic bags filled with samples of foodstuffs can be inserted. In circumferential direction, the elongated openings have a distance from each other such that the plastic bags can be grasped individually by means of the hand 5 or respectively its clamping jaws 8 at the upper rim, and can be lifted out of the magazine. As in the case of the hole magazine 10, a sub-programme makes provision for the control unit 7 to guide the robot 1 or respectively its hand in succession to the next respective magazine opening.

Adjoining the three bag magazines in circumferential direction is a so-called spiral-plater 26. This is an item of apparatus known per se, with a rotatable receiving plate 27 for petri dishes. Over the receiving plate 27, in a manner not shown here in further detail, there is an injection nozzle, which is movable with respect to the receiving plate 27 in radial direction, from which nozzle sample liquid is sprayed, which is to be injected out by means of a dosing pump. Through simultaneous rotation of the receiving plate 27 and radial movement of the injection nozzle, the sample liquid is injected in a spiral path onto the nutrient medium in the petri dish, and namely with a continuously changing injection concentration, which depends upon the respective relative speed between the nozzle and the nutrient medium and also, if applicable, on a corresponding control profile of the dosing pump. The spiral-plater has, in addition, a fixed intermediate deposit site 28 for the petri dish, at which its lid can be removed by means of a suction- and lifting device which is not shown in further detail. Outside the spiral-plater 26 there is a control set 29 which, like all the other items of laboratory apparatus, is connected to the control unit 7. Via corresponding hose connections and hydraulic valves, this brings about on the one hand the "charging" of the spiral-plater with sample liquid, which for this purpose is sucked in through a screen pipette, which is to be explained in further detail, and on the other hand brings about the flushing of the spiral-plater and of the screen pipette with water and disinfection liquid after each completed injection process.

In circumferential direction adjacent to the spiral-plater a large incubator 30 with a door 31 is set up, into which the petri dishes are inserted after injection of the nutrient medium by the robot 1, in, for example, six stacks, whereby the control unit 7 by means of a subprogramme, in turn in an analogous manner to the removal from the hole magazine 10, notes the position of the respective uppermost petri dish in the stack.

Finally, adjacent to the incubator, a mounting is provided for the second hand 6 of the robot 1. This is a universal hand with grippers, which are suited to the handling of the petri dishes and the disposable pipettes. Controlled by the control unit 7, the robot can couple the two hands 5 and 6 selectively with the mounting 4, whereby the respective unused hand remains deposited on the mounting associated therewith, until it is required again.

To carry out a microbiological examination series, for example in a foodstuffs factory, samples of foodstuffs are removed, which have only been roughly estimated as regards their weight, and are filled into the plastic bags. The plastic bags filled with the samples are inserted by hand into the corresponding openings of the bag magazines 23 to 25. Each magazine has, for example, eight openings, so that with, for example, five magazines, up to forty plastic bags can be inserted. In addition, the stack magazines 11, 12 and 13 are filled with petri dishes, in which the nutrient media required for the examination are to be found. Controlled by the correspondingly programmed control unit 7, the samples are now processed fully automatically in succession, and namely in the following sequence of operations:

The robot 1 takes up the hand 5 and moves it to the first plastic bag in the magazine 23. This is grasped between the clamping jaws 8, is lifted out of the magazine, transported to the scales 18 and deposited on its weighing dish by opening the clamping jaws 8. On opening of the clamping jaws, the hand is also moved in vertical direction, in order to ensure that the plastic bag does not remain hanging on the clamping jaws inadvertently. The control unit 7 interrogates as to the weight of the filled plastic bag and determines from this the weight of the sample through subtraction of the known weight of the bag. The bag is now grasped by the hand 8 again, is brought beneath an outlet connection 32 for nutrient solution, provided adjacent to the scales 18 and is opened there. The bag is now filled with nutrient solution. Here, a specified quantity of nutrient solution, corresponding to the determined sample weight, is dosed by the control unit 7, so that the sample and the nutrient solution are in a desired weight ratio. A time-controlled pump is used for dosing.

Then the bag is closed again and is inserted into the opened shaft 17 of the stomacher 16. The bag still remains held by the hand 5, whilst the shaft 17 is closed by motor by means of the shaft flap. At the end of the closure movement, the shaft plate firmly clamps the bag. The hand 5 moves away and the stomacher begins to operate in the manner explained.

In the disinfection- and cleaning bath in the container 14, the screen pipette already mentioned, i.e. a pipette surrounded by a fine mechanical screen, is deposited, which is connected via a hose to the control set 29. The robot 1 travels to the screen pipette, lifts it out of the bath and deposits it on the drip support 15, where the adhering disinfection solution can drip off. Then it returns to the stomacher, grasps the plastic bag there, in the shaft 17 which has opened again in the meantime, and carries the plastic bag over into the stationary holding station 19. On the way there, the robot 1 takes an intermediate stop, at which the plastic bag is opened and is thereby brought to rest, which facilitates the subsequent accurate positioning between the clamping jaws 20 of the stationary holding station 19. After the robot hand 5 has moved away, the plastic bag is now opened in the holding station 19 through moving the clamping jaws 20 apart. In the meantime, the robot fetches the screen pipette from the drip support 15 and carries it, after brief immersion into a washing bath, not shown, into the opened plastic bag. Via the control set 29, a certain quantity of the sample liquid contained in the plastic bag is now sucked into a hose section in the control set 29, keeping back the solid components of the sample. Then the screen pipette is withdrawn again out of the plastic bag and is transported back into the disinfection- and cleaning bath in the container 14. Then the robot 1 exchanges the hand 5 for the hand 6. With the hand 6 it removes a disposable pipette from the hole magazine 10 and then—whilst holding the disposable pipette secure—removes a petri dish from the stack magazine 13. It carries this petri dish to the intermediate deposit site 28 of the spiral plater 26, where the lid of the petri dish is removed, and from there onto the receiving plate 27. There, the nutrient medium of the petri dish is injected, for which the sample liquid contained in the hose section is pressed with hydraulic pressure into the dosing pump of the spiral-plater and is sprayed out by means of the dosing pump through the injection nozzle in the described manner. Whilst the injection process is running, the robot 1 immerses the disposable pipette into the opened plastic bag in the holding station 19 and sucks up further sample liquid therewith. Then the robot moves back to the spiral-plater, grasps the petri dish there, carries it to the intermediate deposit site 28, where the lid is put on again, and brings it from there into the incubator 30 onto one of the three stacks whereby the whole time the filled disposable pipette travels with it. Then a second petri dish is removed from stack magazine 13, is transported to the spiral-plater in the described manner, is opened there and is placed onto the receiving dish 27.

Whilst the second petri dish is injected, the robot moves to one of the two stack magazines 11 or 12. There, by means of a fixed lifting and suction device, the lids of two petri dishes are removed and in each case a new sector of their nutrient medium is injected dropwise out of the disposable pipette. Then the lids are put on again. Then the robot travels with the hand 6 to the stripper 22, by means of which the disposable pipette is stripped off by raising the hand, so that it falls into the waste opening 21. Then the second petri dish, which has been injected in the meantime, is brought from the spiral-plater 26 to the incubator 30. Finally, the plastic bag is freed from the clamping jaws 20 of the holding station 19 and likewise falls into the waste opening 21. The hand 6 is exchanged again for the hand 5 and a new operating cycle can begin. Through a back and forth movement of the sliders of the magazine 13, two new petri dishes are brought into the range of action of the robot 1. When at the end of a cycle all four sectors of the petri dishes from the magazines 11 and 12 are injected, before a changeover of hands, in an interposed operating step the corresponding petri dishes are also transferred into the incubator 30 and new petri dishes are brought into the range of action of the robot 1 by back and forth movement of the sliders of the magazines 11 and 12.

In an alternative to the operating sequence which has been explained, the plastic bags initially remain in the stomacher after the comminution and homogenisation of the sample, so that the sample liquid is removed there from the opened bag. At the end, the plastic bag is thrown directly into the waste opening 21. Through this, the operating sequence is somewhat simpler. On the other hand, the risk of an undesired contamination of the stomacher is somewhat greater.

We claim:

1. Method for supplying a foodstuff sample for microbiological testing, comprising supplying the sample in a plastic bag, adding physiological nutrient solution to the sample in the plastic bag in a specified weight ratio, mechanically comminuting and homogenizing the contents of the bag, removing a partial quantity of the contents of the bag by means of a pipette via a filter as sample liquid, injecting the sample liquid onto at least one nutrient medium situated in a petri dish, and inserting the injected petri dish into an incubator; said method further comprising, in the comminution and homogenization of the contents of the bag, clamping the plastic bag shut and pressing the plastic bag between a fixed jaw and two jaws which oscillate alternately; in the injection of the nutrient medium, injecting the sample liquid out in a spiral shape onto the nutrient medium; employing a laboratory robot system including a laboratory robot to carry out all handling processes by means of a mechanical hand; and controlling the robot and all participating laboratory apparatus with a control unit programmed according to a sequence of examination.

2. Method according to claim 1, wherein the sample in the plastic bag is weighed and the physiological nutrient solution is added respectively in a quantity corresponding to the weight which was determined.

3. Method according to claim 1, wherein the processed plastic bag is transported out of a stomacher where its contents are comminuted and homogenized to a stationary holding device where the sample liquid is removed.

4. Method according to claim 3, wherein the stationary holding device is situated over a waste opening.

5. Method according to claim 3, wherein a pipette is used for the removal of sample liquid, which pipette is surrounded by a mechanical screen, and wherein after each removal operation the pipette is inserted into a disinfection and cleaning bath activated by ultrasonics.

6. Method according to claim 5, wherein the pipette is removed from the disinfection and cleaning bath and is set aside to drip while the stomacher is in operation.

7. Method according to claim 1, wherein the sample liquid is sucked out of the plastic bag into a hose section and is transported therefrom through hydraulic pressure into a dosing pump included in a spiral plater employed for injecting the sample liquid in the spiral shape.

8. Method according to claim 7, wherein in each case after the injecting of the sample liquid, the spiral-plater is flushed with cleaning and disinfection liquids.

9. Method according to claim 1, wherein for the handling of the plastic bags, the laboratory robot uses a hand with two clamping jaws in which openings are provided, which openings are activated by negative pressure to open the plastic bags.

10. Method according to claim 9, wherein an intermediate stop is made during transportation of the plastic bags to steady the movement of the bags, and during the intermediate stop, the plastic bag is opened.

11. Method according to claim 1, wherein additional sample liquid is removed from the plastic bag by means of a disposable suction pipette, and the additional sample liquid is injected out onto at least one nutrient medium in a petri dish, which medium receives injections of several samples.

12. Method according to claim 11, wherein the disposable suction pipette is removed in each case by the laboratory robot from a hole magazine and, after injecting the additional sample liquid, is stripped from the robot hand over a waste opening.

13. Method according to claim 1, wherein petri dishes with fresh nutrient medium are kept in stack magazines from which the dishes are individually advanced by means of a slider into the range of action of the laboratory robot.

14. Method according to claim 13, wherein the petri dishes are closed by lids, which lids are removed by means of suction lifters on a spiral-plater employed for injecting the sample liquid in the spiral shape and/or on the stack magazines, and which lids are subsequently placed in position.

* * * * *